(12) United States Patent
Peters et al.

(10) Patent No.: US 7,220,741 B2
(45) Date of Patent: May 22, 2007

(54) 1,4-DIAZABICYCLOALKANE DERIVATIVES, THEIR PREPARATION AND USE

(75) Inventors: Dan Peters, Ballerup (DK); Gunnar M. Olsen, Ballerup (DK); Elsebet Østergaard Nielsen, Ballerup (DK); Tino Dyhring Jørgensen, Ballerup (DK); Philip K. Ahring, Ballerup (DK)

(73) Assignee: NeuroSearch A/S, Ballerup (DK)

( * ) Notice: Subject to any disclaimer, the term of this patent is extended or adjusted under 35 U.S.C. 154(b) by 0 days.

(21) Appl. No.: 10/528,361

(22) PCT Filed: Sep. 29, 2003

(86) PCT No.: PCT/DK03/00639

§ 371 (c)(1),
(2), (4) Date: Mar. 18, 2005

(87) PCT Pub. No.: WO2004/029053

PCT Pub. Date: Apr. 8, 2004

(65) Prior Publication Data

US 2006/0122172 A1 Jun. 8, 2006

Related U.S. Application Data

(60) Provisional application No. 60/426,368, filed on Nov. 15, 2002.

(30) Foreign Application Priority Data

Sep. 30, 2002 (DK) .......................... PA 2002 01456
Nov. 11, 2002 (DK) .......................... PA 2002 01738

(51) Int. Cl.
*A61P 25/00* (2006.01)
*A61K 31/55* (2006.01)
*C07D 471/08* (2006.01)
*C07D 243/00* (2006.01)
*C07D 221/00* (2006.01)

(52) U.S. Cl. ...................... 514/221; 514/249; 540/472; 540/556; 544/349

(58) Field of Classification Search ................ 514/221, 514/249; 540/472, 556; 544/349
See application file for complete search history.

(56) References Cited

U.S. PATENT DOCUMENTS

| 5,478,939 A | 12/1995 | Trybulski et al. ............ 544/336 |
| 6,407,095 B1 | 6/2002 | Lochead et al. ............. 514/221 |
| 6,998,399 B2 * | 2/2006 | Galli et al. .................. 514/219 |

FOREIGN PATENT DOCUMENTS

| EP | 0 307 140 A | 3/1989 |
| EP | 1 219 622 A | 7/2002 |
| WO | WO-00/34279 A | 6/2000 |
| WO | WO-01/55150 A | 8/2001 |
| WO | WO-01/92259 A | 12/2001 |
| WO | WO-01/92260 A | 12/2001 |
| WO | WO-03/044020 A | 3/2003 |
| WO | WO-03/044019 A1 | 5/2003 |
| WO | WO-03/044024 A1 | 5/2003 |

* cited by examiner

*Primary Examiner*—Brenda Coleman
(74) *Attorney, Agent, or Firm*—Birch, Stewart, Kolasch & Birch, LLP

(57) ABSTRACT

This invention relates to novel 1,4-diazabicycloalkane derivatives and their use in the manufacture of pharmaceutical compositions. The compounds of the invention are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

8 Claims, No Drawings

1,4-DIAZABICYCLOALKANE DERIVATIVES, THEIR PREPARATION AND USE

This application is the National Phase of PCT International application No. PCT/DK2003/000639 filed on Sep. 29, 2003, which claims priority under 35 U.S.C. 119(e) to U.S. Provisional Application No(s). 60/426,3 68 filed on Nov. 15, 2002.

TECHNICAL FIELD

This invention relates to novel 1,4-diazabicycloalkane derivatives and their use in the manufacture of pharmaceutical compositions. The compounds of the invention are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

WO 00/34279 (Sanofi-Synthelabo) describes 1,4-diazabicyclo[3.2.2]nonane derivatives having activity at the nicotinic receptors. Only six-membered heteroaryl derivatives are described. The five-membered heteroaryl derivatives of the present invention have not been described.

WO 01/55150 (Sanofi-Synthelabo) describes 1,4-diazabicyclo[3.2.2]nonane derivatives having activity at the nicotinic receptors. Only bicyclic heteroaryl derivatives are described. The monocyclic heteroaryl derivatives of the present invention have not been described.

WO 01/92259 (Sanofi-Synthelabo) describes 1,4-diazabicyclo[3.2.2]nonane derivatives having activity at the nicotinic receptors. Only phenyl-isoxazole derivatives are described. The thiadiazole derivatives of the present invention have not been described.

WO 01/92260 (Sanofi-Synthelabo) describes 1,4-diazabicyclo[3.2.2]nonane derivatives having activity at the nicotinic receptors. Only phenyl-thiazole derivatives are described. The thiadiazole derivatives of the present invention have not been described.

EP 1219622 (Pfizer Ltd.) describes 1,4-diazabicyclo[3.2.2]nonane derivatives having activity at the nicotinic receptors. Only bicyclic heteroaryl derivatives are described. The monocyclic heteroaryl derivatives of the present invention have not been described.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the monoamine receptors 5-HTR, DAR and NER, and the biogenic amine transporters for 5-HT, DA and NE.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel 1,4-diazabicycloalkane derivatives of Formula I

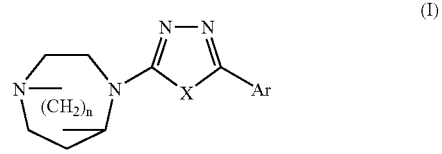

any of its enantiomers or any mixture of its enantiomers, or a pharmaceutically-acceptable addition salt thereof, or an N-oxide thereof, wherein n is 1,2 or 3;

X represents O, S or Se; and

Ar represents a carbocyclic aromatic (aryl) group, or a heterocyclic aromatic (heteroaryl) group, which aromatic group may optionally be substituted one or more times with substituents selected from the group consisting of alkyl, cycloalkyl, cycloalkyl-alkyl, alkenyl, alkynyl, alkoxy, alkoxy-alkyl, alkoxy-alkoxy, cycloalkoxy, cycloalkoxy-alkyl, cycloalkoxy-alkoxy, halogen, $CF_3$, CN, $NO_2$, $NH_2$, carboxy, carbamoyl, amido, sulfamoyl, phenyl and benzyl.

In a second aspect the invention provides pharmaceutical compositions comprising a therapeutically effective amount of the 1,4-diazabicycloalkane derivative of the invention, an enantiomer or a mixture of enantiomers, or a pharmaceutically-acceptable addition salt thereof, together with at least one pharmaceutically-acceptable carrier or diluent.

Viewed from another aspect, the invention relates to the use of a 1,4-diazabicycloalkane derivative of the invention, or an enantiomer or a mixture of enantiomers, or a pharmaceutically-acceptable addition salt thereof, for manufacture of a medicament for the treatment, prevention or alleviation of a disease or a disorder or a condition which is responsive to modulation of cholinergic receptors and/or monoamine receptors.

In yet another aspect the invention provides a method for treatment, prevention or alleviation of a disease or a disorder or a condition of a living animal body, including a human, which disease or disorder is responsive to modulation of cholinergic receptors and/or monoamine receptors, which method comprises the step of administering to such a living animal body, including a human, in need thereof a therapeutically effective amount of a 1,4-diazabicycloalkane derivative of the invention, any of its enantiomers or any mixture of its enantiomers, or a pharmaceutically-acceptable addition salt thereof.

Other objects of the invention will be apparent to the person skilled in the art from the following detailed description and examples.

DETAILED DISCLOSURE OF THE INVENTION

In its first aspect the present invention provides novel 1,4-diazabicycloalkane derivatives represented by the general Formula I

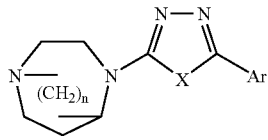

(I)

any of its enantiomers or any mixture of its enantiomers, or a pharmaceutically-acceptable addition salt thereof, or an N-oxide thereof, wherein n is 1, 2 or 3;

X represents O, S or Se; and

Ar represents a carbocyclic aromatic (aryl) group, or a heterocyclic aromatic (heteroaryl) group, which aromatic group may optionally be substituted one or more times with substituents selected from the group consisting of alkyl, cycloalkyl, cycloalkyl-alkyl, alkenyl, alkynyl, alkoxy, alkoxy-alkyl, alkoxy-alkoxy, cycloalkoxy, cycloalkoxy-alkyl, cycloalkoxy-alkoxy, halogen, $CF_3$, CN, $NO_2$, $NH_2$, carboxy, carbamoyl, amido, sulfamoyl, phenyl and benzyl.

In a more preferred embodiment Ar represents a carbocyclic aromatic (aryl) group, or a heterocyclic aromatic (heteroaryl) group, which aromatic group may optionally be substituted one or more times with substituents selected from the group consisting of alkyl, alkoxy, halogen, $CF_3$, CN, $NO_2$, $NH_2$ and phenyl.

In a first preferred embodiment the compound of the invention is a 1,4-diazabicyclo[3.2.2]nonane derivative represented by Formula II

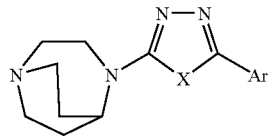

(II)

wherein
X and Ar are as defined above.

In a more preferred embodiment the compound of the invention is a 4-thiadiazolyl-1,4-diazabicyclo[3.2.2]nonane derivative represented by Formula III

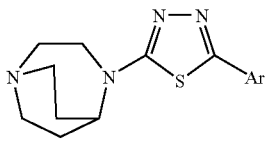

(III)

wherein Ar is as defined above.

In another preferred embodiment the compound of the invention is a 4-oxadiazolyl-1,4-diazabicyclo[3.2.2]nonane derivative represented by Formula IV

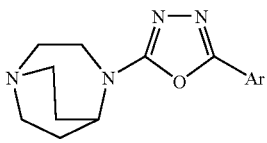

(IV)

wherein Ar is as defined above.

In a second preferred embodiment the carbocyclic aromatic (aryl) group is an optionally substituted phenyl, indenyl, naphthyl, azulenyl, fluorenyl, or anthracenyl group.

In a more preferred embodiment the carbocyclic aromatic group is phenyl, optionally substituted one or two times with substituents selected from the group consisting of alkyl, cycloalkyl, cycloalkyl-alkyl, alkoxy, cycloalkoxy, halogen, $CF_3$, CN, $NO_2$, $NH_2$, carboxy, carbamoyl, amido, sulfamoyl, phenyl and benzyl.

In an even more preferred embodiment the carbocyclic aromatic group is phenyl, optionally substituted one or two times with substituents selected from the group consisting of alkyl, alkoxy, halogen, $CF_3$, CN, $NO_2$, $NH_2$, and phenyl.

In a most preferred embodiment the 4-thiadiazolyl-1,4-diazabicyclo[3.2.2]nonane derivative of the invention is 4-(5-Phenyl-1,3,4-thiadiazol-2-yl)-1,4-diazabicyclo [3.2.2]nonane;

or an enantiomer or a mixture of enantiomers, or a pharmaceutically-acceptable addition salt thereof, or an N-oxide thereof;

and the 4-oxadiazolyl-1,4-diazabicyclo[3.2.2]nonane derivative of the invention is 4-(5-Phenyl-1,3,4-oxadiazol-2-yl)-1,4-diazabicyclo[3.2.2] nonane;

4-[5-(3-Methoxyphenyl)-1,3,4-oxadiazol-2-yl]-1,4-diazabicyclo[3.2.2]nonane;

4-[5-(4-Methoxyphenyl)-1,3,4-oxadiazol-2-yl]-1,4-diazabicyclo[3.2.2]nonane;

4-[5-(4-Chlorophenyl)-1,3,4-oxadiazol-2-yl]-1,4-diazabicyclo[3.2.2]nonane;

4-[5-(4-Phenyl-phenyl)-1,3,4-oxadiazol-2-yl]-1,4-diazabicyclo[3.2.2]nonane;

or

4-[5-(2-Naphthyl)-1,3,4-oxadiazol-2-yl]-1,4-diazabicyclo[3.2.2]nonane;

or an enantiomer or a mixture of enantiomers, or a pharmaceutically-acceptable addition salt thereof, or an N-oxide thereof.

In a third preferred embodiment the heterocyclic aromatic (heteroaryl) group is an optionally substituted aromatic monocyclic heterocyclic group, or an optionally substituted aromatic bi- or poly-heterocyclic heterocyclic group, which heterocyclic groups include benzo-fused 5- and 6-membered heterocyclic rings containing one or more heteroatoms, selected from nitrogen (N), oxygen (O), sulphur (S) and/or selen (Se).

In a more preferred embodiment the aromatic monocyclic heterocyclic group is an optionally substituted aromatic 5- or 6-membered heterocyclic monocyclic group.

In an even more preferred embodiment the optionally substituted aromatic monocyclic heterocyclic group is furanyl, in particular 2-furanyl or 3-furanyl; thienyl, in particular 2-thienyl or 3-thienyl; selenophenyl, in particular 2-selenophenyl or 3-selenophenyl; pyrrolyl (azolyl), in particular 2-pyrrolyl or 3-pyrrolyl; oxazolyl, in particular oxazol-2-, 4- or 5-yl; thiazolyl, in particular thiazol-2-, 4- or 5-yl; imidazolyl, in particular 2-imidazolyl or 4-imidazolyl; pyrazolyl, in particular 3-pyrazolyl or 4-pyrazolyl; isoxazolyl, in particular isoxazol-3-, 4- or 5-yl; isothiazolyl, in particular isothiazol-3-, 4- or 5-yl; oxadiazolyl, in particular 1,2,3-oxadiazol-4- or 5-yl, or 1,3,4-oxadiazol-2-yl; triazolyl, in particular 1,2,3-triazol-4-yl or 1,2,4-triazol-3-yl; thiadiazolyl, in particular 1,2,3-thiadiazol-4- or 5-yl, or 1,3,4-thiadiazol-2-yl; pyridinyl, in particular 2-, 3- or 4-pyridinyl; pyridazinyl, in particular 3- or 4-pyridazinyl; pyrimidinyl, in particular 2-, 4- or 5-pyrimidinyl; pyrazinyl, in particular 2- or 3-pyrazinyl; and triazinyl, in particular 1,2,4- or 1,3,5-triazinyl.

In another preferred embodiment the compound of the invention is a 4-thiadiazolyl-1,4-diazabicyclo[3.2.2]nonane derivative of Formula III, wherein Ar represents an optionally substituted aromatic monocyclic heterocyclic group selected from selenophenyl, in particular 2-selenophenyl or 3-selenophenyl; imidazolyl, in particular 2-imidazolyl, 4-imidazolyl or 5-imidazolyl; pyrazolyl, in particular 3-pyrazolyl, 4-pyrazolyl or 5-pyrazolyl; thiazolyl, in particular 2-thiazolyl or 5-thiazolyl; isothiazolyl, in particular 3-isothiazolyl, 4-isothiazolyl or 5-isothiazolyl; oxadiazolyl, in particular 1,2,3-oxadiazol-4-yl, 1,2,3-oxadiazol-5-yl or 1,3,4-oxadiazol-2-yl; furazanyl, in particular 3-furazanyl; triazolyl, in particular 1,2,3-triazol-4-yl, 1,2,3-triazol-5-yl, 1,2,4-triazol-3-yl or 1,2,4-triazol-5-yl; thiadiazolyl, in particular 1,3,4-thiadiazol-2-yl, 1,2,4-thiadiazol-3-yl or 1,2,4-thiadiazol-5-yl; pyridazinyl, in particular 3-pyridazinyl or 4-pyridazinyl; and triazinyl, in particular 1,3,5-triazin-2-yl.

In a more preferred embodiment the aromatic 5- or 6-membered heterocyclic monocyclic group is optionally substituted one or two times with substituents selected from the group consisting of alkyl, alkoxy, halogen, CF$_3$, CN, NO$_2$, NH$_2$ and phenyl.

In a most preferred embodiment the 4-thiadiazolyl-1,4-diazabicyclo[3.2.2]nonane derivative of the invention is 4-[5-(2-Selenophenyl)-1,3,4-thiadiazol-2-yl]-1,4-diazabicyclo[3.2.2]nonane;

4-[5-(3-Selenophenyl)-1,3,4-thiadiazol-2-yl]-1,4-diazabicyclo[3.2.2]nonane;

4-[5-(2-Imidazolyl)-1,3,4-thiadiazol-2-yl]-1,4-diazabicyclo[3.2.2]nonane;

4-[5-(4-Imidazolyl)-1,3,4-thiadiazol-2-yl]-1,4-diazabicyclo[3.2.2]nonane;

4-[5-(5-Imidazolyl)-1,3,4-thiadiazol-2-yl]-1,4-diazabicyclo[3.2.2]nonane;

4-[5-(1-Methyl-2-imidazolyl)-1,3,4-thiadiazol-2-yl]-1,4-diazabicyclo[3.2.2]nonane;

4-[5-(1-Methyl-4-imidazolyl)-1,3,4-thiadiazol-2-yl]-1,4-diazabicyclo[3.2.2]nonane;

4-[5-(1-Methyl-5-imidazolyl)-1,3,4-thiadiazol-2-yl]-1,4-diazabicyclo[3.2.2]nonane;

4-[5-(3-Pyrazolyl)-1,3,4-thiadiazol-2-yl]-1,4-diazabicyclo[3.2.2]nonane;

4-[5-(4-Pyrazolyl)-1,3,4-thiadiazol-2-yl]-1,4-diazabicyclo[3.2.2]nonane;

4-[5-(5-Pyrazolyl)-1,3,4-thiadiazol-2-yl]-1,4-diazabicyclo[3.2.2]nonane;

4-[5-(1-Methyl-3-pyrazolyl)-1,3,4-thiadiazol-2-yl]-1,4-diazabicyclo[3.2.2]nonane;

4-[5-(1-Methyl-4-pyrazolyl)-1,3,4-thiadiazol-2-yl]-1,4-diazabicyclo[3.2.2]nonane;

4-[5-(1-Methyl-5-pyrazolyl)-1,3,4-thiadiazol-2-yl]-1,4-diazabicyclo[3.2.2]nonane;

4-[5-(2-Thiazolyl)-1,3,4-thiadiazol-2-yl]-1,4-diazabicyclo[3.2.2]nonane;

4-[5-(4-Thiazolyl)-1,3,4-thiadiazol-2-yl]-1,4-diazabicyclo[3.2.2]nonane;

4-[5-(5-Thiazolyl)-1,3,4-thiadiazol-2-yl]-1,4-diazabicyclo[3.2.2]nonane;

4-[5-(3-Isothiazolyl)-1,3,4-thiadiazol-2-yl]-1,4-diazabicyclo[3.2.2]nonane;

4-[5-(4-Isothiazolyl)-1,3,4-thiadiazol-2-yl]-1,4-diazabicyclo[3.2.2]nonane;

4-[5-(5-Isothiazolyl)-1,3,4-thiadiazol-2-yl]-1,4-diazabicyclo[3.2.2]nonane;

4-[5-(1,2,3-Oxadizol-4-yl)-1,3,4-thiadiazol-2-yl]-1,4-diazabicyclo[3.2.2]nonane;

4-[5-(1,2,3-Oxadizol-5-yl)-1,3,4-thiadiazol-2-yl]-1,4-diazabicyclo[3.2.2]nonane;

4-[1,3,4-Oxadizol-2-yl)-1,3,4-thiadiazol-2-yl]-1,4-diazabicyclo[3.2.2]nonane;

4-[5-(3-Furazanyl)-1,3,4-thiadiazol-2-yl]-1,4-diazabicyclo[3.2.2]nonane;

4-[5-(1,2,3-Triazol-4-yl)-1,3,4-thiadiazol-2-yl]-1,4-diazabicyclo[3.2.2]nonane;

4-[5-(1,2,3-Triazol-5-yl)-1,3,4-thiadiazol-2-yl]-1,4-diazabicyclo[3.2.2]nonane;

4-[5-(1-Methyl-1,2,3-triazol-4-yl)-1,3,4-thiadiazol-2-yl]-1,4-diazabicyclo[3.2.2]nonane;

4-[5-(1-Methyl-1,2,3-triazol-5-yl)-1,3,4-thiadiazol-2-yl]-1,4-diazabicyclo[3.2.2]nonane;

4-[5-(1,2,4-Triazol-3-yl)-1,3,4-thiadiazol-2-yl]-1,4-diazabicyclo[3.2.2]nonane;

4-[5-(1,2,4-Triazol-5-yl)-1,3,4-thiadiazol-2-yl]-1,4-diazabicyclo[3.2.2]nonane;

4-[5-(1-Methyl-1,2,4-triazol-3-yl)-1,3,4-thiadiazol-2-yl]-1,4-diazabicyclo[3.2.2]nonane;

4-[5-(1-Methyl-1,2,4-triazol-5-yl)-1,3,4-thiadiazol-2-yl]-1,4-diazabicyclo[3.2.2]nonane;

4-[5-(1,3,4-Thiadiazol-2-yl)-1,3,4-thiadiazol-2-yl]-1,4-diazabicyclo[3.2.2]nonane;

4-[5-(1,2,4-Thiadiazol-3-yl)-1,3,4-thiadiazol-2-yl]-1,4-diazabicyclo[3.2.2]nonane;

4-[5-(1,2,4-Thiadiazol-5-yl)-1,3,4-thiadiazol-2-yl]-1,4-diazabicyclo[3.2.2]nonane;
4-[5-(3-Pyridazinyl)-1,3,4-thiadiazol-2-yl]-1,4-diazabicyclo[3.2.2]nonane;
4-[5-(4-Pyridazinyl)-1,3,4-thiadiazol-2-yl]-1,4-diazabicyclo[3.2.2]nonane; or
4-[5-(1,3,5-Triazin-2-yl)-1,3,4-thiadiazol-2-yl]-1,4-diazabicyclo[3.2.2]nonane;

or an enantiomer or a mixture of its enantiomers, or a pharmaceutically-acceptable addition salt thereof, or an N-oxide thereof.

In yet another preferred embodiment the compound of the invention is a 4-oxadiazolyl-1,4-diazabicyclo[3.2.2]nonane derivative of Formula IV, wherein Ar represents an optionally substituted aromatic monocyclic heterocyclic group selected from furyl, in particular 2-furyl or 3-furyl; pyridyl, in particular 2-pyridyl, 3-pyridyl or 4-pyridyl; thienyl, in particular 2-thienyl or 3-thienyl; pyrrolyl, in particular 2-pyrrolyl or 3-pyrrolyl; pyrimidinyl, in particular 2-pyrimidinyl, 4-pyrimidinyl or 5-pyrimidinyl; pyrazinyl; selenophenyl, in particular 2-selenophenyl or 3-selenophenyl; oxazolyl, in particular 2-oxazolyl, 4-oxazolyl or 5-oxazolyl; isoxazolyl, in particular 3-isoxazolyl, 4-isoxazolyl or 5-isoxazolyl; imidazolyl, in particular 2-imidazolyl, 4-imidazolyl or 5-imidazolyl; pyrazolyl, in particular 3-pyrazolyl, 4-pyrazolyl or 5-pyrazolyl; thiazolyl, in particular 2-thiazolyl, 4-thiazolyl or 5-thiazolyl; isothiazolyl, in particular 3-isothiazolyl, 4-isothiazolyl or 5-isothiazolyl; oxadiazolyl, in particular 1,2,3-oxadiazol4-yl, 1,2,3-oxadiazol-5-yl or 1,3,4-oxadiazol-2-yl; furazanyl, in particular 3-furazanyl; triazolyl, in particular 1,2,3-triazol-4-yl, 1,2,3-triazol-5-yl, 1,2,4-triazol-3-yl or 1,2,4-triazol-5-yl; thiadiazolyl, in particular 1,3,4-thiadiazol-2-yl, 1,2,4-thiadiazol-3-yl or 1,2,4-thiadiazol-5-yl; pyridazinyl, in particular 3-pyridazinyl or 4-pyridazinyl; and triazinyl, in particular 1,3,5-triazin-2-yl.

In a most preferred embodiment the 4-oxadiazolyl-1,4-diazabicyclo[3.2.2]nonane derivative of the invention is
4-[5-(2-Furyl)-1,3,4-oxadiazol-2-yl]-1,4-diazabicyclo[3.2.2]nonane;
4-[5-(3-Furyl)-1,3,4-oxadiazol-2-yl]-1,4-diazabicyclo[3.2.2]nonane;
4-[5-(2-Pyridyl)-1,3,4-oxadiazol-2-yl]-1,4-diazabicyclo[3.2.2]nonane;
4-[5-(3-Pyridyl)-1,3,4-oxadiazol-2-yl]-1,4-diazabicyclo[3.2.2]nonane;
4-[5-(4-Pyridyl)-1,3,4-oxadiazol-2-yl]-1,4-diazabicyclo[3.2.2]nonane;
4-[5-(2-Thienyl)-1,3,4-oxadiazol-2-yl]-1,4-diazabicyclo[3.2.2]nonane;
4-[5-(3-Thienyl)-1,3,4-oxadiazol-2-yl]-1,4-diazabicyclo[3.2.2]nonane;
4-[5-(2-Pyrrolyl)-1,3,4-oxadiazol-2-yl]-1,4-diazabicyclo[3.2.2]nonane;
4-[5-(3-Pyrrolyl)-1,3,4-oxadiazol-2-yl]-1,4-diazabicyclo[3.2.2]nonane;
4-[5-(1-Methyl-2-pyrrolyl)-1,3,4-oxadiazol-2-yl]-1,4-diazabicyclo[3.2.2]nonane;
4-[5-(1-Methyl-3-pyrrolyl)-1,3,4-oxadiazol-2-yl]-1,4-diazabicyclo[3.2.2]nonane;
4-[5-(2-Pyrimidinyl)-1,3,4-oxadiazol-2-yl]-1,4-diazabicyclo[3.2.2]nonane;
4-[5-(4-Pyrimidinyl)-1,3,4-oxadiazol-2-yl]-1,4-diazabicyclo[3.2.2]nonane;
4-[5-(5-Pyrimidinyl)-1,3,4-oxadiazol-2-yl]-1,4-diazabicyclo[3.2.2]nonane;
4-[5-(Pyrazinyl)-1,3,4-oxadiazol-2-yl]-1,4-diazabicyclo[3.2.2]nonane;
4-[5-(2-Selenophenyl)-1,3,4-oxadiazol-2-yl]-1,4-diazabicyclo[3.2.2]nonane;
4-[5-(3-Selenophenyl)-1,3,4-oxadiazol-2-yl]-1,4-diazabicyclo[3.2.2]nonane;
4-[5-(2-Oxazolyl)-1,3,4-oxadiazol-2-yl]-1,4-diazabicyclo[3.2.2]nonane;
4-[5-(4-Oxazolyl)-1,3,4-oxadiazol-2-yl]-1,4-diazabicyclo[3.2.2]nonane;
4-[5-(5-Oxazolyl)-1,3,4-oxadiazol-2-yl]-1,4-diazabicyclo[3.2.2]nonane;
4-[5-(3-Isoxazolyl)-1,3,4-oxadiazol-2-yl]-1,4-diazabicyclo[3.2.2]nonane;
4-[5-(4-Isoxazolyl)-1,3,4-oxadiazol-2-yl]-1,4-diazabicyclo[3.2.2]nonane;
4-[5-(5-Isoxazolyl)-1,3,4-oxadiazol-2-yl]-1,4-diazabicyclo[3.2.2]nonane;
4-[5-(2-Imidazolyl)-1,3,4-oxadiazol-2-yl]-1,4-diazabicyclo[3.2.2]nonane;
4-[5-(4-Imidazolyl)-1,3,4-oxadiazol-2-yl]-1,4-diazabicyclo[3.2.2]nonane;
4-[5-(5-Imidazolyl)-1,3,4-oxadiazol-2-yl]-1,4-diazabicyclo[3.2.2]nonane;
4-[5-(1-Methyl-2-imidazolyl)-1,3,4-oxadiazol-2-yl]-1,4-diazabicyclo[3.2.2]nonane;
4-[5-(1-Methyl-4-imidazolyl)-1,3,4-oxadiazol-2-yl]-1,4-diazabicyclo[3.2.2]nonane;
4-[5-(1-Methyl-5-imidazolyl)-1,3,4-oxadiazol-2-yl]-1,4-diazabicyclo[3.2.2]nonane;
4-[5-(3-Pyrazolyl)-1,3,4-oxadiazol-2-yl]-1,4-diazabicyclo[3.2.2]nonane;
4-[5-(4-Pyrazolyl)-1,3,4-oxadiazol-2-yl]-1,4-diazabicyclo[3.2.2]nonane;
4-[5-(5-Pyrazolyl)-1,3,4-oxadiazol-2-yl]-1,4-diazabicyclo[3.2.2]nonane;
4-[5-(1-Methyl-3-pyrazolyl)-1,3,4-oxadiazol-2-yl]-1,4-diazabicyclo[3.2.2]nonane;
4-[5-(1-Methyl-4-pyrazolyl)-1,3,4-oxadiazol-2-yl]-1,4-diazabicyclo[3.2.2]nonane;
4-[5-(1-Methyl-5-pyrazolyl)-1,3,4-oxadiazol-2-yl]-1,4-diazabicyclo[3.2.2]nonane;
4-[5-(2-Thiazolyl)-1,3,4-oxadiazol-2-yl]-1,4-diazabicyclo[3.2.2]nonane;
4-[5-(4-Thiazolyl)-1,3,4-oxadiazol-2-yl]-1,4-diazabicyclo[3.2.2]nonane;
4-[5-(5-Thiazolyl)-1,3,4-oxadiazol-2-yl]-1,4-diazabicyclo[3.2.2]nonane;
4-[5-(3-Isothiazolyl)-1,3,4-oxadiazol-2-yl]-1,4-diazabicyclo[3.2.2]nonane;
4-[5-(4-Isothiazolyl)-1,3,4-oxadiazol-2-yl]-1,4-diazabicyclo[3.2.2]nonane;
4-[5-(5-Isothiazolyl)-1,3,4-oxadiazol-2-yl]-1,4-diazabicyclo[3.2.2]nonane;
4-[5-(1,2,3-Oxadizol-4-yl)-1,3,4-oxadiazol-2-yl]-1,4-diazabicyclo[3.2.2]nonane;
4-[5-(1,2,3-Oxadizol-5-yl)-1,3,4-oxadiazol-2-yl]-1,4-diazabicyclo[3.2.2]nonane;
4-[5-(1,3,4-Oxadizol-2-yl)-1,3,4-oxadiazol-2-yl]-1,4-diazabicyclo[3.2.2]nonane;
4-[5-(3-Furazanyl)-1,3,4-oxadiazol-2-yl]-1,4-diazabicyclo[3.2.2]nonane;
4-[5-(1,2,3-Triazol-4-yl)-1,3,4-oxadiazol-2-yl]-1,4-diazabicyclo[3.2.2]nonane;
4-[5-(1,2,3-Triazol-5-yl)-1,3,4-oxadiazol-2-yl]-1,4-diazabicyclo[3.2.2]nonane;
4-[5-(1-Methyl-1,2,3-triazol-4-yl)-1,3,4-oxadiazol-2-yl]-1,4-diazabicyclo[3.2.2]nonane;

4-[5-(1-Methyl-1,2,3-triazol-5-yl)-1,3,4-oxadiazol-2-yl]-1,
4-diazabicyclo[3.2.2]nonane;
4-[5-(1,2,4-Triazol-3-yl)-1,3,4-oxadiazol-2-yl]-1,4-diazabi-
cyclo[3.2.2]nonane;
4-[5-(1,2,4-Triazol-5-yl)-1,3,4-oxadiazol-2-yl]-1,4-diazabi-
cyclo[3.2.2]nonane;
4-[5-(1-Methyl-1,2,4-triazol-3-yl)-1,3,4-oxadiazol-2-yl]-1,
4-diazabicyclo[3.2.2]nonane;
4-[5-(1-Methyl-1,2,4-triazol-5-yl)-1,3,4-oxadiazol-2-yl]-1,
4-diazabicyclo[3.2.2]nonane;
4-[5-(1,3,4-Thiadiazol-2-yl)-1,3,4-oxadiazol-2-yl]-1,4-diaz-
abicyclo[3.2.2]nonane;
4-[5-(1,2,4-Thiadiazol-3-yl)-1,3,4-oxadiazol-2-yl]-1,4-diaz-
abicyclo[3.2.2]nonane;
4-[5-(1,2,4-Thiadiazol-5-yl)-1,3,4-oxadiazol-2-yl]-1,4-diaz-
abicyclo[3.2.2]nonane;
4-[5-(3-Pyridazinyl)-1,3,4-oxadiazol-2-yl]-1,4-diazabicyclo
[3.2.2]nonane;
4-[5-(4-Pyridazinyl)-1,3,4-oxadiazol-2-yl]-1,4-diazabicyclo
[3.2.2]nonane; or
4-[5-(1,3,5-Triazin-2-yl)-1,3,4-oxadiazol-2-yl]-1,4-diazabi-
cyclo[3.2.2]nonane;

or an enantiomer or a mixture of its enantiomers, or a pharmaceutically-acceptable addition salt thereof, or an N-oxide thereof.

In a fourth preferred embodiment the optionally substituted bicyclic aromatic heterocyclic group is indolyl, in particular 2-indolyl or 3-indolyl; isoindolyl, in particular 1-isoindolyl or 3-isoindolyl; benzo[b]furanyl, in particular 2-benzo[b]furanyl or 3-benzo[b]furanyl; benzo[b]thienyl, in particular 2-benzo[b]thienyl or 3-benzo[b]thienyl; benzoimidazolyl, in particular 2-benzoimidazolyl; benzothiazolyl, in particular 2-benzothiazolyl; quinolinyl, in particular 2-quinolinyl, 3-quinolinyl or 4-quinolinyl; isoquinolinyl, in particular 1-isoquinolinyl, 3-isoquinolinyl or 4-isoquinolinyl; cinnolinyl, in particular 3-cinnolinyl or 4-cinnolinyl; phthalazinyl, in particular 1-phthalazinyl or 4-phthalazinyl; quinazolinyl, in particular 2-quinazolinyl or 4-quinazolinyl; quinoxalinyl, in particular 2-quinoxalinyl or 3-quinoxalinyl.

In a more preferred embodiment the optionally substituted polycyclic aromatic heterocyclic group is a tricyclic heteroaryl groups, in particular 2-acridinyl, 3-acridinyl, 6-acridinyl or 7-acridinyl; carbazolyl, in particular 2-carbazolyl, 3-carbazolyl, 6-carbazolyl or 7-carbazolyl; phenazinyl, in particular 2-phenazinyl, 3-phenazinyl, 7-phenazinyl or 8-phenazinyl; phenothiazinyl, in particular 2-phenothiazinyl, 3-phenothiazinyl, 7-phenothiazinyl or 8-phenothiazinyl; and phenoxazinyl, in particular 2-phenoxazinyl, 3-phenoxazinyl, 7-phenoxazinyl or 8-phenoxazinyl.

In an even more preferred embodiment the compound of the invention is a 4-thiadiazolyl-1,4-diazabicyclo[3.2.2] nonane derivative of Formula III, wherein the polycyclic aromatic heterocyclic group is an optionally substituted bicyclic heteroaryl selected from quinolinyl, in particular 2-quinolinyl or 3-quinolinyl; isoquinolinyl, in particular 3-isoquinolinyl; cinnolinyl, in particular 3-cinnolinyl; indolizinyl, in particular 2-indolizinyl; benzimidazolyl, in particular 2-benzimidazolyl; benzothiazolyl, in particular 2-benzothiazolyl; phthalazinyl, in particular 7-phthalazinyl; quinazolinyl, in particular 2-quinazolinyl, quinoxalinyl, in particular 2-quinoxalinyl; naphthyridinyl, in particular 1,8-naphthyridin-2-yl or 1,8-naphthyridin-3-yl; and acridinyl, in particular 2-acridinyl or 3-acridinyl.

In a yet more preferred embodiment the bicyclic heteroaryl group is optionally substituted one or two times with substituents selected from the group consisting of alkyl, alkoxy, halogen, $CF_3$, CN, $NO_2$, $NH_2$, and phenyl.

In a most preferred embodiment the 4-thiadiazdlyl-1,4-diazabicyclo[3.2.2]nonane derivative of the invention is
4-[5-(2-Quinolinyl)-1,3,4-thiadiazol-2-yl]-1,4-diazabicyclo
[3.2.2]nonane;
4-[5-(3-Quinolinyl)-1,3,4-thiadiazol-2-yl]-1,4-diazabicyclo
[3.2.2]nonane;
4-[5-(3-Isoquinolinyl)-1,3,4-thiadiazol-2-yl]-1,4-diazabicy-
clo[3.2.2]nonane;
4-[5-(3-Cinnolinyl)-1,3,4-thiadiazol-2-yl]-1,4-diazabicyclo
[3.2.2]nonane;
4-[5-(2-Indolizinyl)-1,3,4-thiadiazol-2-yl]-1,4-diazabicyclo
[3.2.2]nonane;
4-[5-(1-Methyl-2-indolyl)-1,3,4-thiadiazol-2-yl]-1,4-diaz-
abicyclo[3.2.2]nonane;
4-[5-(2-Benzimidazolyl)-1,3,4-thiadiazol-2-yl]-1,4-diazabi-
cyclo[3.2.2]nonane;
4-[5-(1-Methyl-2-benzimidazolyl)-1,3,4-thiadiazol-2-yl]-1,
4-diazabicyclo[3.2.2]nonane;
4-[5-(2-Benzothiazolyl)-1,3,4-thiadiazol-2-yl]-1,4-diazabi-
cyclo[3.2.2]nonane;
4-[5-(7-Phtalazinolinyl)-1,3,4-thiadiazol-2-yl]-1,4-diazabi-
cyclo[3.2.2]nonane;
4-[5-(2-Quinazolinyl)-1,3,4-thiadiazol-2-yl]-1,4-diazabicy-
clo[3.2.2]nonane;
4-[5-(2-Quinoxalinyl)-1,3,4-thiadiazol-2-yl]-1,4-diazabicy-
clo[3.2.2]nonane;
4-[5-(1,8-Naphthyridin-2-yl)-1,3,4-thiadiazol-2-yl]-1,4-di-
azabicyclo[3.2.2]nonane;
4-[5-(1,8-Naphthyridin-3-yl)-1,3,4-thiadiazol-2-yl]-1,4-di-
azabicyclo[3.2.2]nonane;
4-[5-(2-Acridinyl)-1,3,4-thiadiazol-2-yl]-1,4-diazabicyclo
[3.2.2]nonane; or
4-[5-(3-Acridinyl)-1,3,4-thiadiazol-2-yl]-1,4-diazabicyclo
[3.2.2]nonane;

or an enantiomer or a mixture of its enantiomers, or a pharmaceutically-acceptable addition salt thereof, or an N-oxide thereof.

In yet another preferred embodiment the compound of the invention is a 4-oxadiazolyl-1,4-diazabicyclo[3.2.2]nonane derivative of Formula IV, wherein Ar represents an optionally substituted aromatic monocyclic heterocyclic group selected from benzothienyl, in particular 2-benzothienyl, 3-benzothienyl, 5-benzothienyl or 6-benzothienyl; benzofuryl, in particular 2-benzofuryl, 3-benzofuryl, 5-benzofuryl or 6-benzofuryl; quinolinyl, in particular 2-quinolinyl or 3-quinolinyl; isoquinolinyl, in particular 3-isoquinolinyl; cinnolinyl, in particular 3-cinnolinyl; indolizinyl, in particular 2-indolizinyl; indolyl, in particular 2-indolyl; benzimidazolyl, in particular 2-benzimidazolyl; benzothiazolyl, in particular 2-benzothiazolyl; phthalazinyl, in particular 7-phthalazinyl; quinazolinyl, in particular 2-quinazolinyl; quinoxalinyl, in particular 2-quinoxalinyl; naphthyridinyl, in particular 1,8-naphthyridin-2-yl or 1,8-naphthyridin-3-yl; acridinyl, in particular 2-acridinyl or 3-acridinyl; dibenzofuryl, in particular 2-dibenzofuryl, or 3-dibenzofuryl; dibenzothienyl, in particular 2-dibenzothienyl or 3-dibenzothienyl; phenoxazinyl, in particular 2-phenoxazinyl or 3-phenoxazinyl.

In a still more preferred embodiment the aromatic monocyclic heterocyclic group is optionally substituted one or two times with substituents selected from the group consisting of alkyl, alkoxy, halogen, $CF_3$, CN, $NO_2$, $NH_2$, and phenyl.

In a most preferred embodiment the compound of the invention is
4-[5-(2-Benzothienyl)-1,3,4-oxadiazol-2-yl]-1,4-diazabicy-
clo[3.2.2]nonane;

4-[5-(3-Benzothienyl)-1,3,4-oxadiazol-2-yl]-1,4-diazabicyclo[3.2.2]nonane;
4-[5-(5-Benzothienyl)-1,3,4-oxadiazol-2-yl]-1,4-diazabicyclo[3.2.2]nonane;
4-[5-(6-Benzothienyl)-1,3,4-oxadiazol-2-yl]-1,4-diazabicyclo[3.2.2]nonane;
4-[5-(2-Benzofuryl)-1,3,4-oxadiazol-2-yl]-1,4-diazabicyclo[3.2.2]nonane;
4-[5-(3-Benzofuryl)-1,3,4-oxadiazol-2-yl]-1,4-diazabicyclo[3.2.2]nonane;
4-[5-(5-Benzofuryl)-1,3,4-oxadiazol-2-yl]-1,4-diazabicyclo[3.2.2]nonane;
4-[5-(6-Benzofuryl)-1,3,4-oxadiazol-2-yl]-1,4-diazabicyclo[3.2.2]nonane;
4-[5-(2-Quinolinyl)-1,3,4-oxadiazol-2-yl]-1,4-diazabicyclo[3.2.2]nonane;
4-[5-(3-Quinolinyl)-1,3,4-oxadiazol-2-yl]-1,4-diazabicyclo[3.2.2]nonane;
4-[5-(3-Isoquinolinyl)-1,3,4-oxadiazol-2-yl]-1,4-diazabicyclo[3.2.2]nonane;
4-[5-(3-Cinnolinyl)-1,3,4-oxadiazol-2-yl]-1,4-diazabicyclo[3.2.2]nonane;
4-[5-(2-Indolizinyl)-1,3,4-oxadiazol-2-yl]-1,4-diazabicyclo[3.2.2]nonane;
4-[5-(2-Indolyl)-1,3,4-oxadiazol-2-yl]-1,4-diazabicyclo[3.2.2]nonane;
4-[5-(1-Methyl-2-indolyl)-1,3,4-oxadiazol-2-yl]-1,4-diazabicyclo[3.2.2]nonane;
4-[5-(2-Benzimidazolyl)-1,3,4-oxadiazol-2-yl]-1,4-diazabicyclo[3.2.2]nonane;
4-[5-(1-Methyl-2-benzimidazolyl)-1,3,4-oxadiazol-2-yl]-1,4-diazabicyclo[3.2.2]nonane;
4-[5-(2-Benzothiazolyl)-1,3,4-oxadiazol-2-yl]-1,4-diazabicyclo[3.2.2]nonane;
4-[5-(7-Phtalazinolinyl)-1,3,4-oxadiazol-2-yl]-1,4-diazabicyclo[3.2.2]nonane;
4-[5-(2-Quinazolinyl)-1,3,4-oxadiazol-2-yl]-1,4-diazabicyclo[3.2.2]nonane;
4-[5-(2-Quinoxalinyl)-1,3,4-oxadiazol-2-yl]-1,4-diazabicyclo[3.2.2]nonane;
4-[5-(1,8-Naphthyridin-2-yl)-1,3,4-oxadiazol-2-yl]-1,4-diazabicyclo[3.2.2]nonane;
4-[5-(1,8-Naphthyridin-3-yl)-1,3,4-oxadiazol-2-yl]-1,4-diazabicyclo[3.2.2]nonane;
4-[5-(2-Acridinyl)-1,3,4-oxadiazol-2-yl]-1,4-diazabicyclo[3.2.2]nonane;
4-[5-(3-Acridinyl)-1,3,4-oxadiazol-2-yl]-1,4-diazabicyclo[3.2.2]nonane;
4-[5-(2-Dibenzofuryl)-1,3,4-oxadiazol-2-yl]-1,4-diazabicyclo[3.2.2]nonane;
4-[5-(3-Dibenzofuryl)-1,3,4-oxadiazol-2-yl]-1,4-diazabicyclo[3.2.2]nonane;
4-[5-(2-Dibenzothienyl)-1,3,4-oxadiazol-2-yl]-1,4-diazabicyclo[3.2.2]nonane;
4-[5-(3-Dibenzothienyl)-1,3,4-oxadiazol-2-yl]-1,4-diazabicyclo[3.2.2]nonane;
4-[5-(2-Phenoxazinyl)-1,3,4-oxadiazol-2-yl]-1,4-diazabicyclo[3.2.2]nonane;

or

4-[5-(3-Phenoxazinyl)-1,3,4-oxadiazol-2-yl]-1,4-diazabicyclo[3.2.2]nonane;

or an enantiomer or a mixture of its enantiomers, or a pharmaceutically-acceptable addition salt thereof, or an N-oxide thereof.

Any combination of two or more of the embodiments described herein is considered within the scope of the present invention.

Definition of Substituents

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl (allyl); 1-, 2- or 3-butenyl, or 1,3-butdienyl; 1-, 2-, 3-, 4- or 5-hexenyl, or 1,3-hexdienyl, or 1,3,5-hextrienyl; 1-, 2-, 3-, 4-, 5-, 6-, or 7-octenyl, or 1,3-octdienyl, or 1,3,5-octtrienyl, or 1,3,5,7-octtetraenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-henynyl, or 1,3-hexdiynyl or 1,3,5-hextriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5octtriynyl, or 1,3,5,7-octtetraenyl.

In the context of this invention an alkoxy group designates an "alkyl-O—" group, wherein alkyl is as defined above. Examples of preferred alkoxy groups of the invention include methoxy and ethoxy.

In the context of this invention an alkoxy-alkyl group designates an "alkyl-O-alkyl" group, wherein alkyl is as defined above. Examples of preferred alkoxy-alkyl groups of the invention include methoxy-methyl, methoxy-ethyl, ethoxy-methyl, and ethoxy-ethyl.

In the context of this invention an alkoxy-alkoxy group designates an "alkyl-O-alkyl-O—" group, wherein alkyl is as defined above. Examples of preferred alkoxy-alkoxy groups of the invention include methoxy-methoxy, methoxy-ethoxy, ethoxy-methoxy, and ethoxy-ethoxy.

In the context of this invention a cycloalkoxy group designates a "cycloalkyl-O—" group, wherein cycloalkyl is as defined above.

In the context of this invention a cycloalkoxy-alkyl group designates a "cycloalkyl-O-alkyl" group, wherein cycloalkyl and alkyl are as defined above.

In the context of this invention a cycloalkoxy-alkoxy group designates a "cycloalkyl-O-alkyl-O—" group, wherein cycloalkyl and alkyl are as defined above.

In the context of this invention halogen represents a fluorine, a chlorine, a bromine or an iodine atom. Thus, a trihalogenmethyl group represents e.g. a trifluoromethyl group, a trichloromethyl group and similar trihalogen-substituted methyl groups.

In the context of this invention an acyl group designates a carboxy group (—COOH) or an alkyl-carbonyl group (alkyl-CO—), wherein alkyl is as defined above. Examples of preferred acyl groups of the invention include carboxy, acetyl, and propionyl.

Pharmaceutically Acceptable Salts

The 1,4-diazabicycloalkane derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a 1,4-diazabicycloalkane derivative of the invention and its pharmaceutically acceptable acid addition salt.

Metal salts of a 1,4-diazabicycloalkane derivative of the invention include alkali metal salts such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, in particular the methyl-onium salt, the cycloalkyl-onium salts, and the cycloalkylalkyl-onium salts.

Steric Isomers

The 1,4-diazabicycloalkane derivative of the present invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The 1,4-diazabicycloalkane derivative of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Preparation

The 1,4-diazabicycloalkane derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention relates to novel 1,4-diazabicycloalkane derivatives found to be cholinergic ligands at the nicotinic acetylcholine receptors (nAChR) and modulators of the monoamine receptors, in particular the biogenic amine transporters 5-HT, DA and NE. Moreover, preferred compounds of the invention show selective α7 activity.

In the context of this invention the term "modulator" covers agonists, partial agonists, antagonists and allosteric modulators of the receptor.

Due to their pharmacological profile the 1,4-diazabicycloalkane derivatives of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the 1,4-diazabicycloalkane derivatives of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the 1,4-diazabicycloalkane derivatives of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the 1,4-diazabicycloalkane derivatives of the invention may be useful for the treatment of endocrine disorders, such as thyrotoxicosis, pheochromocytoma, hypertension and arrhythmias.

In still another preferred embodiment the 1,4-diazabicycloalkane derivatives of the invention may be useful for the treatment of neurodegenerative disorders, including transient anoxia and induced neuro-degeneration.

In even another preferred embodiment the 1,4-diazabicycloalkane derivatives of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the 1,4-diazabicycloalkane derivatives of the invention may be useful for the treatment of mild, moderate or even severe pain of acute, chronic or recurrent character, as well as pain caused by migraine, postoperative pain, and phantom limb pain.

Finally the 1,4-diazabicycloalkane derivatives of the invention may be useful for the treatment of withdrawal symptoms caused by termination of use of addictive substances. Such addictive substances include nicotine-containing products such as tobacco, opioids such as, heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the 1,4-diazabicycloalkane derivatives of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of the 1,4-diazabicycloalkane derivative of the invention.

While a 1,4-diazabicycloalkane derivative of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 1,4-diazabicycloalkane derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in drage, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The 1,4-diazabicycloalkane derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of a 1,4-diazabicycloalkane derivative of the invention.

In a preferred embodiment, the disease, disorder or condition relates to the central nervous system.

In a preferred embodiment, the disease, disorder or condition is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a another preferred embodiment, the disease, disorder or condition are associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In a third preferred embodiment, the disease, disorder or condition is related to the endocrine system, such as thyrotoxicosis, pheochromocytoma, hypertension and arrhythmias.

In a fourth preferred embodiment, the disease, disorder or condition is a neurodegenerative disorders, including transient anoxia and induced neuro-degeneration.

In a fifth preferred embodiment, the disease, disorder or condition is an inflammatory disorder, including inflammatory skin disorders such as acne and rosacea, Chron's disease, inflammatory bowel disease, ulcerative colitis, and diarrhoea.

In a sixth preferred embodiment, the disease, disorder or condition is mild, moderate or even severe pain of acute, chronic or recurrent character, as well as pain caused by migraine, postoperative pain, and phantom limb pain.

In a seventh preferred embodiment, the disease, disorder or condition is associated with withdrawal symptoms caused by termination of use of addictive substances, including nicotine-containing products such as tobacco, opioids such as heroin, cocaine and morphine, benzodiazepines and benzodiazepine-like drugs, and alcohol.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulfate was used as drying agent in the workup-procedures and solvents were evaporated under reduced pressure.

1,4-Diazabicyclo[3.2.2]nonane (Intermediate compound) was prepared according to *J. Med. Chem.* 1993 36 2311–2320, and according to the following slightly modified method.

To the solution of 1,4-diazabicyclo[3.2.2]nonan-3-one (15.8 g, 113 mmol) in absolute dioxane (130 ml) LiAlH$_4$ (4.9 g, 130 mmol) was added under argon. The mixture was refluxed for 6 hours and then allowed to reach room temperature. Water (5 ml in 10 ml of dioxane) was added by drops to the reaction mixture, the mixture was stirred for 0.5 hour and then filtered off via glass filter. The solvent was evaporated and the residue was distilled using Kugelrohr apparatus at 90° C. (0.1 mbar) to yield 1,4-diazabicyclo [3.2.2]nonane (11.1 g, 78%) as colourless hygroscopic material.

1,4-Diazabicyclo[3.2.2]nonan-3-one (Intermediate compound)

To the solution of 3-quinuclidinone hydrochloride (45 g, 278 mmol) in 90 ml of water, hydroxylamine hydrochloride (21 g, 302 mmol) and sodium acetate (CH$_3$COOHx3H$_2$O, 83 g, 610 mmol) were added, the mixture was stirred at 70° C. for 1 hour and then cooled to 0° C. The separated crystalline material was filtered off (without washing!) and dried in vacuo to yield 40.0 g of oxime.

The 3-quinuclidinone oxime (40.0 g) was added during 2 hours by small portions to polyphosphoric acid* (190 g, prepared as described below*), preheated to 120° C. The temperature of the solution during the reaction was kept at 130° C. After addition of all oxime the solution was stirred for 20 minutes at the same temperature, then transferred to an enamelled vessel and allowed to reach room temperature. The acidic mixture was neutralized by a solution of potassium carbonate (500 g in 300 ml of water), transferred into 2000 ml flask, diluted with 300 ml of water and extracted with chloroform (3×600 ml). The combined organic extracts were dried with sodium sulphate, the solvent evaporated and the solid residue dried up in vacuo to yield 30.0 g (77%) of the mixture of lactams.

Crystallization of the obtained mixture from 1,4-dioxane (220 ml) gave 15.8 g (40.5%) of 1,4-diazabicyclo[3.2.2] nonan-3-one as colourless large crystals with mp 211–212° C.

The filtrate was evaporated and the residue was chromatographed on a silica gel (Merck, 9385, 230–400 mesh) column with acetone as eluent. The solvent was evaporated and the residue recrystallized from ethyl etanoate to yield 1,3-diazabicyclo[3.2.2]nonan-4-one (10.2 g, 26%) as colourless fine crystals with mp 125–126° C.

Polyphosphoric Acid*

85% Orthophosphoric acid (500 g, 294 ml, 4.337 mol) was placed into 2000 ml flask and then phosphor pentoxide (750 g, 5.284 mol) was added at room temperature (ratio acid-pentoxide, 2:3). The mixture was stirred at 200–220° C. for 2 hours to yield of 1250 g of polyphosphoric acid, containing 80% of $P_2O_5$.

2-Chloro-5-phenyl-1,3,4-thiadiazole (Intermediate compound)

2-Amino-5-phenyl-1,3,4-thiadiazole sulfate (25.12 g, 142 mmol) was stirred in concentrated hydrochloric acid (300 ml) at 0° C. Sodium nitrite (12.7 g, 184 mmol) was added during a period of 10 minutes. The reaction mixture was stirred at 50° C. for 15 hours. The hydrochloric acid was evaporated. Aqueous sodium hydroxide (4 M, 250 ml) was added and the the precipitate was filtered. Chromatography on silica gel with ethyl acetate as solvent gave a pure product. Yield 15.5 g (56%).

Method A 4-(5-Phenyl-1,3,4-thiadiazol-2-yl)-1,4-diazabicyclo [3.2.2]nonane fumaric acid salt (Compound A1);

A mixture of 1,4-diazabicyclo[3.2.2]nonane (1.28 g, 10.2 mmol), 2-chloro-5-phenyl-1,3,4-thiadiazole (2.00 g, 10.2 mmol), triethylamine (2.83 ml, 20.3 mmol) and dioxane (20 ml) was stirred at reflux for 70 hours. Aqueous sodium hydroxide (1 M, 25 ml) was added and the mixture was extracted twice with ethyl acetate (2×20 ml). Chromatography on silica gel with dichloromethane, 10% methanol and 1% aqueous ammonia as solvent gave the title compound as an oil. The corresponding salt was obtained by addition of a diethyl ether and methanol mixture (9:1) saturated with fumaric acid. Yield 0.95 g, 23%. Mp 150.9° C.

The following compounds are prepared in a similar manner:

4-[5-(2-Selenophenyl)-1,3,4-thiadiazol-2-yl]-1,4-diazabicyclo[3.2.2]nonane (Compound A2);
4-[5-(3-Selenophenyl)-1,3,4-thiadiazol-2-yl]-1,4-diazabicyclo[3.2.2]nonane (Compound A3);
4-[5-(2-Imidazolyl)-1,3,4-thiadiazol-2-yl]-1,4-diazabicyclo[3.2.2]nonane (Compound A4);
4-[5-(4-Imidazolyl)-1,3,4-thiadiazol-2-yl]-1,4-diazabicyclo[3.2.2]nonane (Compound A5);
4-[5-(5-Imidazolyl)-1,3,4-thiadiazol-2-yl]-1,4-diazabicyclo[3.2.2]nonane (Compound A6);
4-[5-(1-Methyl-2-imidazolyl)-1,3,4-thiadiazol-2-yl]-1,4-diazabicyclo[3.2.2]nonane (Compound A7);
4-[5-(1-Methyl-4-imidazolyl)-1,3,4-thiadiazol-2-yl]-1,4-diazabicyclo[3.2.2]nonane (Compound A8);
4-[5-(1-Methyl-5-imidazolyl)-1,3,4-thiadiazol-2-yl]-1,4-diazabicyclo[3.2.2]nonane (Compound A9);
4-[5-(3-Pyrazolyl)-1,3,4-thiadiazol-2-yl]-1,4-diazabicyclo[3.2.2]nonane (Compound A10);
4-[5-(4-Pyrazolyl)-1,3,4-thiadiazol-2-yl]-1,4-diazabicyclo[3.2.2]nonane (Compound A11);
4-[5-(5-Pyrazolyl)-1,3,4-thiadiazol-2-yl]-1,4-diazabicyclo[3.2.2]nonane (Compound A12);
4-[5-(1-Methyl-3-pyrazolyl)-1,3,4-thiadiazol-2-yl]-1,4-diazabicyclo[3.2.2]nonane (Compound A13);
4-[5-(1-Methyl-4-pyrazolyl)-1,3,4-thiadiazol-2-yl]-1,4-diazabicyclo[3.2.2]nonane (Compound A14);
4-[5-(1-Methyl-5-pyrazolyl)-1,3,4-thiadiazol-2-yl]-1,4-diazabicyclo[3.2.2]nonane (Compound A15);
4-[5-(2-Thiazolyl)-1,3,4-thiadiazol-2-yl]-1,4-diazabicyclo [3.2.2]nonane (Compound A16);
4-[5-(4-Thiazolyl)-1,3,4-thiadiazol-2-yl]-1,4-diazabicyclo [3.2.2]nonane (Compound A17);
4-[5-(5-Thiazolyl)-1,3,4-thiadiazol-2-yl]-1,4-diazabicyclo [3.2.2]nonane (Compound A18);
4-[5-(3-Isothiazolyl)-1,3,4-thiadiazol-2-yl]-1,4-diazabicyclo[3.2.2]nonane (Compound A19);
4-[5-(4-Isothiazolyl)-1,3,4-thiadiazol-2-yl]-1,4-diazabicyclo[3.2.2]nonane (Compound A20);
4-[5-(5-isothiazolyl)-1,3,4-thiadiazol-2-yl]-1,4-diazabicyclo[3.2.2]nonane (Compound A21);
4-[5-(1,2,3-Oxadizol-4-yl)-1,3,4-thiadiazol-2-yl]-1,4-diazabicyclo[3.2.2]nonane (Compound A22);
4-[5-(1,2,3-Oxadizol-5-yl)-1,3,4-thiadiazol-2-yl]-1,4-diazabicyclo[3.2.2]nonane (Compound A23);
4-[1,3,4-Oxadizol-2-yl)-1,3,4-thiadiazol-2-yl]-1,4-diazabicyclo[3.2.2]nonane (Compound A24);
4-[5-(3-Furazanyl)-1,3,4-thiadiazol-2-yl]-1,4-diazabicyclo [3.2.2]nonane (Compound A25);
4-[5-(1,2,3-Triazol-4-yl)-1,3,4-thiadiazol-2-yl]-1,4-diazabicyclo[3.2.2]nonane (Compound A26);
4-[5-(1,2,3-Triazol-5-yl)-1,3,4-thiadiazol-2-yl]-1,4-diazabicyclo[3.2.2]nonane (Compound A27);
4-[5-(1-Methyl-1,2,3-triazol-4-yl)-1,3,4-thiadiazol-2-yl]-1,4-diazabicyclo[3.2.2]nonane (Compound A28);
4-[5-(1-Methyl-1,2,3-triazol-5-yl)-1,3,4-thiadiazol-2-yl]-1,4-diazabicyclo[3.2.2]nonane (Compound A29);
4-[5-(1,2,4-Triazol-3-yl)-1,3,4-thiadiazol-2-yl]-1,4-diazabicyclo[3.2.2]nonane (Compound A30);
4-[5-(1,2,4-Triazol-5-yl)-1,3,4-thiadiazol-2-yl]-1,4-diazabicyclo[3.2.2]nonane (Compound A31);
4-[5-(1-Methyl-1,2,4-triazol-3-yl)-1,3,4-thiadiazol-2-yl]-1,4-diazabicyclo[3.2.2]nonane (Compound A32);
4-[5-(1-Methyl-1,2,4-triazol-5-yl)-1,3,4-thiadiazol-2-yl]-1,4-diazabicyclo[3.2.2]nonane (Compound A33);
4-[5-(1,3,4-Thiadiazol-2-yl)-1,3,4-thiadiazol-2-yl]-1,4-diazabicyclo[3.2.2]nonane (Compound A34);
4-[5-(1,2,4-Thiadiazol-3-yl)-1,3,4-thiadiazol-2-yl]-1,4-diazabicyclo[3.2.2]nonane (Compound A35);
4-[5-(1,2,4-Thiadiazol-5-yl)-1,3,4-thiadiazol-2-yl]-1,4-diazabicyclo[3.2.2]nonane (Compound A36);
4-[5-(3-Pyridazinyl)-1,3,4-thiadiazol-2-yl]-1,4-diazabicyclo [3.2.2]nonane (Compound A37);
4-[5-(4-Pyridazinyl)-1,3,4-thiadiazol-2-yl]-1,4-diazabicyclo [3.2.2]nonane (Compound A38);
4-[5-(1,3,5-Triazin-2-yl)-1,3,4-thiadiazol-2-yl]-1,4-diazabicyclo[3.2.2]nonane (Compound A39);
4-[5-(2-Quinolinyl)-1,3,4-thiadiazol-2-yl]-1,4-diazabicyclo [3.2.2]nonane (Compound A40);
4-[5-(3-Quinolinyl)-1,3,4-thiadiazol-2-yl]-1,4-diazabicyclo [3.2.2]nonane (Compound A41);
4-[5-(3-Isoquinolinyl)-1,3,4-thiadiazol-2-yl]-1,4-diazabicyclo[3.2.2]nonane (Compound A42);
4-[5-(3-Cinnolinyl)-1,3,4-thiadiazol-2-yl]-1,4-diazabicyclo [3.2.2]nonane (Compound A43);
4-[5-(2-Indolizinyl)-1,3,4-thiadiazol-2-yl]-1,4-diazabicyclo [3.2.2]nonane (Compound A44);
4-[5-(2-Indolyl)-1,3,4-thiadiazol-2-yl]-1,4-diazabicyclo [3.2.2]nonane (Compound A45);
4-[5-(1-Methyl-2-indolyl)-1,3,4-thiadiazol-2-yl]-1,4-diazabicyclo[3.2.2]nonane (Compound A46);
4-[5-(2-Benzimidazolyl)-1,3,4-thiadiazol-2-yl]-1,4-diazabicyclo[3.2.2]nonane (Compound A47);
4-[5-(1-Methyl-2-benzimidazolyl)-1,3,4-thiadiazol-2-yl]-1,4-diazabicyclo[3.2.2]nonane (Compound A48);

4-[5-(2-Benzothiazolyl)-1,3,4-thiadiazol-2-yl]-1,4-diazabicyclo[3.2.2]nonane (Compound A49);
4-[5-(7-Phtalazinolinyl)-1,3,4-thiadiazol-2-yl]-1,4-diazabicyclo[3.2.2]nonane (Compound A50);
4-[5-(2-Quinazolinyl)-1,3,4-thiadiazol-2-yl]-1,4-diazabicyclo[3.2.2]nonane (Compound A51);
4-[5-(2-Quinoxalinyl)-1,3,4-thiadiazol-2-yl]-1,4-diazabicyclo[3.2.2]nonane (Compound A52);
4-[5-(1,8-Naphthyridin-2-yl)-1,3,4-thiadiazol-2-yl]-1,4-diazabicyclo[3.2.2]nonane (Compound A53);
4-[5-(1,8-Naphthyridin-3-yl)-1,3,4-thiadiazol-2-yl]-1,4-diazabicyclo[3.2.2]nonane (Compound A54);
4-[5-(2-Acridinyl)-1,3,4-thiadiazol-2-yl]-1,4-diazabicyclo[3.2.2]nonane (Compound A55); and
4-[5-(3-Acridinyl)-1,3,4-thiadiazol-2-yl]-1,4-diazabicyclo[3.2.2]nonane (Compound A56).

Method B

2-Mercaptobenzyl-5-phenyl-1,3,4-oxadiazole (Intermediate compound)

Benzylbromide (16.8 ml, 141 mmol) was added over a time period of 10 minutes to a mixture of 5-phenyl-1,3,4-oxadiazole-2-thiol (commercially available) (25.2 g, 141 mmol), triethylamine (19.7 ml, 141 mmol) and ethanol (250 ml) at room temperature.

The mixture was allowed to stir at room temperature for 3 hours. Aqueous sodium hydroxide (1 M, 250 ml) was added and the mixture was extracted twice with dichloromethane (2×200 ml). Chromatography on silica gel with dichloromethane, 10% methanol and 1% aqueous ammonia as solvent gave the title compound as an oil. Yield 34.2 g (90%).

Method C 5-(2-Furyl)-1,3,4-oxadiazole-2-thiol (Intermediate compound)

Carbon disuldide (16.5 g, 216 mmol) was added to a mixture of 2-furoic hydrazide (13.6 g, 108 mmol), potassium hydroxide (6.68 g, 119 mmol) and methanol (125 ml). The mixture was allowed to stir at room temperature for 30 minutes followed by reflux for 8 hours. The methanol was evaporated. The aqueous phase was acidified to pH=4 with concentrated hydrochloric acid. The product was isolated by filtration. Yield 12.9 g (72%).

Method D 4-(5-Phenyl-1,3,4-oxadiazol-2-yl)-1,4-diazabicyclo[3.2.2]nonane fumaric acid salt (Compound D1)

A mixture of 2-mercaptobenzyl-5-phenyl-1,3,4-oxadiazole (Method B) (1.0 g, 3.7 mmol), 1,4-diazabicyclo[3.2.2]nonane (0.47 g, 3.7 mmol) and diisopropylethylamine (1.3 ml, 7.4 mmol) was stirred over for 4 days at 100° C. Aqueous sodium hydroxide (1 M, 25 ml) was added and the mixture was extracted twice with dichloromethane (2×20 ml). Chromatography on silica gel with dichloromethane, 10% methanol and 1% aqueous ammonia as solvent gave the title compound as an oil. The corresponding salt was obtained by addition of a diethyl ether and methanol mixture (9:1) saturated with fumaric acid. Yield 0.47 g, 33%. Mp 176.6–178.8° C.

The following compounds are prepared in a similar manner:

4-[5-(2-Furyl)-1,3,4-oxadiazol-2-yl]-1,4-diazabicyclo[3.2.2]nonane fumaric acid salt (Compound D2)

Was prepared according to Method D. Mp 175° C.

4-[5-(4-Methoxyphenyl)-1,3,4-oxadiazol-2-yl]-1,4-diazabicyclo[3.2.2]nonane fumaric acid salt (Compound D3)

Was prepared according to Method D. Mp 190.1–191.2° C.

4-[5-(4-Pyridyl)-1,3,4-oxadiazol-2-yl]-1,4-diazabicyclo[3.2.2]nonane fumaric acid salt (Compound D4)

Was prepared according to Method D. Mp 165.9–166.8° C.

4-[5-(2-Thienyl)-1,3,4-oxadiazol-2-yl]-1,4-diazabicyclo[3.2.2]nonane fumaric acid salt (Compound D5)

Was prepared according to Method D. Mp 161.8–162.7° C.

4-[5-(3-Pyridyl)-1,3,4-oxadiazol-2-yl]-1,4-diazabicyclo[3.2.2]nonane fumaric acid salt (Compound D6)

Was prepared according to Method D. Mp 176.8–177.5° C.

4-[5-(4-Chlorophenyl)-1,3,4-oxadiazol-2-yl]-1,4-diazabicyclo[3.2.2]nonane fumaric acid salt (Compound D7)

Was prepared according to Method D. Mp 184.3–185.8° C.

4-[5-(3-Methoxyphenyl)-1,3,4-oxadiazol-2-yl]-1,4-diazabicyclo[3.2.2]nonane fumaric acid salt (Compound D8)

Was prepared according to Method D. Mp 126–164° C.

4-[5-(4-Phenyl-phenyl)-1,3,4-oxadiazol-2-yl]-1,4-diazabicyclo[3.2.2]nonane fumaric acid salt (Compound D9)

Was prepared according to Method D. Mp 238–239° C.

4-[5-(2-Naphthyl)-1,3,4-oxadiazol-2-yl]-1,4-diazabicyclo[3.2.2]nonane fumaric acid salt (Compound D10)

Was prepared according to Method D. Mp 194.6–195.7° C.

In analogy herewith the following compounds are prepared:
4-[5-(3-Furyl)-1,3,4-oxadiazol-2-yl]-1,4-diazabicyclo[3.2.2]nonane (Compound D11);
4-[5-(3-Thienyl)-1,3,4-oxadiazol-2-yl]-1,4-diazabicyclo[3.2.2]nonane (Compound D12);
4-[5-(2-Pyridyl)-1,3,4-oxadiazol-2-yl]-1,4-diazabicyclo[3.2.2]nonane (Compound D13);

4-[5-(2-Pyrrolyl)-1,3,4-oxadiazol-2-yl]-1,4-diazabicyclo[3.2.2]nonane (Compound D14);
4-[5-(3-Pyrrolyl)-1,3,4-oxadiazol-2-yl]-1,4-diazabicyclo[3.2.2]nonane (Compound D15);
4-[5-(1-Methyl-2-pyrrolyl)-1,3,4-oxadiazol-2-yl]-1,4-diazabicyclo[3.2.2]nonane (Compound D16);
4-[5-(1-Methyl-3-pyrrolyl)-1,3,4-oxadiazol-2-yl]-1,4-diazabicyclo[3.2.2]nonane (Compound D17);
4-[5-(2-Pyrimidinyl)-1,3,4-oxadiazol-2-yl]-1,4-diazabicyclo[3.2.2]nonane (Compound D18);
4-[5-(4-Pyrimidinyl)-1,3,4-oxadiazol-2-yl]-1,4-diazabicyclo[3.2.2]nonane (Compound D19);
4-[5-(5-Pyrimidinyl)-1,3,4-oxadiazol-2-yl]-1,4-diazabicyclo[3.2.2]nonane (Compound D20);
4-[5-(Pyrazinyl)-1,3,4-oxadiazol-2-yl]-1,4-diazabicyclo[3.2.2]nonane (Compound D21);
4-[5-(2-Selenophenyl)-1,3,4-oxadiazol-2-yl]-1,4-diazabicyclo[3.2.2]nonane (Compound D22);
4-[5-(3-Selenophenyl)-1,3,4-oxadiazol-2-yl]-1,4-diazabicyclo[3.2.2]nonane (Compound D23);
4-[5-(2-Oxazolyl)-1,3,4-oxadiazol-2-yl]-1,4-diazabicyclo[3.2.2]nonane (Compound D24);
4-[5-(4-Oxazolyl)-1,3,4-oxadiazol-2-yl]-1,4-diazabicyclo[3.2.2]nonane (Compound D25);
4-[5-(5-Oxazolyl)-1,3,4-oxadiazol-2-yl]-1,4-diazabicyclo[3.2.2]nonane (Compound D26);
4-[5-(3-Isoxazolyl)-1,3,4-oxadiazol-2-yl]-1,4-diazabicyclo[3.2.2]nonane (Compound D27);
4-[5-(4-Isoxazolyl)-1,3,4-oxadiazol-2-yl]-1,4-diazabicyclo[3.2.2]nonane (Compound D28);
4-[5-(5-Isoxazolyl)-1,3,4-oxadiazol-2-yl]-1,4-diazabicyclo[3.2.2]nonane (Compound 29);
4-[5-(2-Imidazolyl)-1,3,4-oxadiazol-2-yl]-1,4-diazabicyclo[3.2.2]nonane (Compound D30);
4-[5-(4-Imidazolyl)-1,3,4-oxadiazol-2-yl]-1,4-diazabicyclo[3.2.2]nonane (Compound D31);
4-[5-(5-Imidazolyl)-1,3,4-oxadiazol-2-yl]-1,4-diazabicyclo[3.2.2]nonane (Compound D32);
4-[5-(1-Methyl-2-imidazolyl)-1,3,4-oxadiazol-2-yl]-1,4-diazabicyclo[3.2.2]nonane (Compound D33);
4-[5-(1-Methyl-4-imidazolyl)-1,3,4-oxadiazol-2-yl]-1,4-diazabicyclo[3.2.2]nonane (Compound D34);
4-[5-(1-Methyl-5-imidazolyl)-1,3,4-oxadiazol-2-yl]-1,4-diazabicyclo[3.2.2]nonane (Compound D35);
4-[5-(3-Pyrazolyl)-1,3,4-oxadiazol-2-yl]-1,4-diazabicyclo[3.2.2]nonane (Compound D36);
4-[5-(4-Pyrazolyl)-1,3,4-oxadiazol-2-yl]-1,4-diazabicyclo[3.2.2]nonane (Compound D37);
4-[5-(5-Pyrazolyl)-1,3,4-oxadiazol-2-yl]-1,4-diazabicyclo[3.2.2]nonane (Compound D38);
4-[5-(1-Methyl-3-pyrazolyl)-1,3,4-oxadiazol-2-yl]-1,4-diazabicyclo[3.2.2]nonane (Compound D39);
4-[5-(1-Methyl-4-pyrazolyl)-1,3,4-oxadiazol-2-yl]-1,4-diazabicyclo[3.2.2]nonane (Compound D40);
4-[5-(1-Methyl-5-pyrazolyl)-1,3,4-oxadiazol-2-yl]-1,4-diazabicyclo[3.2.2]nonane (Compound D41);
4-[5-(2-Thiazolyl)-1,3,4-oxadiazol-2-yl]-1,4-diazabicyclo[3.2.2]nonane (Compound D42);
4-[5-(4-Thiazolyl)-1,3,4-oxadiazol-2-yl]-1,4-diazabicyclo[3.2.2]nonane (Compound D43);
4-[5-(5-Thiazolyl)-1,3,4-oxadiazol-2-yl]-1,4-diazabicyclo[3.2.2]nonane (Compound D44);
4-[5-(3-Isothiazolyl)-1,3,4-oxadiazol-2-yl]-1,4-diazabicyclo[3.2.2]nonane (Compound D45);
4-[5-(4-Isothiazolyl)-1,3,4-oxadiazol-2-yl]-1,4-diazabicyclo[3.2.2]nonane (Compound D46);
4-[5-(5-Isothiazolyl)-1,3,4-oxadiazol-2-yl]-1,4-diazabicyclo[3.2.2]nonane (Compound D47);
4-[5-(1,2,3-Oxadizol-4-yl)-1,3,4-oxadiazol-2-yl]-1,4-diazabicyclo[3.2.2]nonane (Compound D48);
4-[5-(1,2,3-Oxadizol-5-yl)-1,3,4-oxadiazol-2-yl]-1,4-diazabicyclo[3.2.2]nonane (Compound D49);
4-[5-(1,3,4-Oxadizol-2-yl)-1,3,4-oxadiazol-2-yl]-1,4-diazabicyclo[3.2.2]nonane (Compound D50);
4-[5-(3-Furazanyl)-1,3,4-oxadiazol-2-yl]-1,4-diazabicyclo[3.2.2]nonane (Compound D51);
4-[5-(1,2,3-Triazol-4-yl)-1,3,4-oxadiazol-2-yl]-1,4-diazabicyclo[3.2.2]nonane (Compound D52);
4-[5-(1,2,3-Triazol-5-yl)-1,3,4-oxadiazol-2-yl]-1,4-diazabicyclo[3.2.2]nonane (Compound D53);
4-[5-(1-Methyl-1,2,3-triazol-4-yl)-1,3,4-oxadiazol-2-yl]-1,4-diazabicyclo[3.2.2]nonane (Compound D54);
4-[5-(1-Methyl-1,2,3-triazol-5-yl)-1,3,4-oxadiazol-2-yl]-1,4-diazabicyclo[3.2.2]nonane (Compound D55);
4-[5-(1,2,4-Triazol-3-yl)-1,3,4-oxadiazol-2-yl]-1,4-diazabicyclo[3.2.2]nonane (Compound D56);
4-[5-(1,2,4-Triazol-5-yl)-1,3,4-oxadiazol-2-yl]-1,4-diazabicyclo[3.2.2]nonane (Compound D57);
4-[5-(1-Methyl-1,2,4-triazol-3-yl)-1,3,4-oxadiazol-2-yl]-1,4-diazabicyclo[3.2.2]nonane (Compound D58);
4-[5-(1-Methyl-1,2,4-triazol-5-yl)-1,3,4-oxadiazol-2-yl]-1,4-diazabicyclo[3.2.2]nonane (Compound D59);
4-[5-(1,3,4-Thiadiazol-2-yl)-1,3,4-oxadiazol-2-yl]-1,4-diazabicyclo[3.2.2]nonane (Compound D60);
4-[5-(1,2,4-Thiadiazol-3-yl)-1,3,4-oxadiazol-2-yl]-1,4-diazabicyclo[3.2.2]nonane (Compound D61);
4-[5-(1,2,4-Thiadiazol-5-yl)-1,3,4-oxadiazol-2-yl]-1,4-diazabicyclo[3.2.2]nonane (Compound D62);
4-[5-(3-Pyridazinyl)-1,3,4-oxadiazol-2-yl]-1,4-diazabicyclo[3.2.2]nonane (Compound D63);
4-[5-(4-Pyridazinyl)-1,3,4-oxadiazol-2-yl]-1,4-diazabicyclo[3.2.2]nonane (Compound D64);
4-[5-(1,3,5-Triazin-2-yl)-1,3,4-oxadiazol-2-yl]-1,4-diazabicyclo[3.2.2]nonane (Compound D65);
4-[5-(2-Benzothienyl)-1,3,4-oxadiazol-2-yl]-1,4-diazabicyclo[3.2.2]nonane (Compound D66);
4-[5-(3-Benzothienyl)-1,3,4-oxadiazol-2-yl]-1,4-diazabicyclo[3.2.2]nonane (Compound D67);
4-[5-(5-Benzothienyl)-1,3,4-oxadiazol-2-yl]-1,4-diazabicyclo[3.2.2]nonane (Compound D68);
4-[5-(6-Benzothienyl)-1,3,4-oxadiazol-2-yl]-1,4-diazabicyclo[3.2.2]nonane (Compound D69);
4-[5-(2-Benzofuryl)-1,3,4-oxadiazol-2-yl]-1,4-diazabicyclo[3.2.2]nonane (Compound D70);
4-[5-(3-Benzofuryl)-1,3,4-oxadiazol-2-yl]-1,4-diazabicyclo[3.2.2]nonane (Compound D71);
4-[5-(5-Benzofuryl)-1,3,4-oxadiazol-2-yl]-1,4-diazabicyclo[3.2.2]nonane (Compound D72);
4-[5-(6-Benzofuryl)-1,3,4-oxadiazol-2-yl]-1,4-diazabicyclo[3.2.2]nonane (Compound D73);
4-[5-(2-Quinolinyl)-1,3,4-oxadiazol-2-yl]-1,4-diazabicyclo[3.2.2]nonane (Compound D74);
4-[5-(3-Quinolinyl)-1,3,4-oxadiazol-2-yl]-1,4-diazabicyclo[3.2.2]nonane (Compound D75);
4-[5-(3-Isoquinolinyl)-1,3,4-oxadiazol-2-yl]-1,4-diazabicyclo[3.2.2]nonane (Compound D76);
4-[5-(3-Cinnolinyl)-1,3,4-oxadiazol-2-yl]-1,4-diazabicyclo[3.2.2]nonane (Compound D77);
4-[5-(2-Indolizinyl)-1,3,4-oxadiazol-2-yl]-1,4-diazabicyclo[3.2.2]nonane (Compound D78);
4-[5-(2-Indolyl)-1,3,4-oxadiazol-2-yl]-1,4-diazabicyclo[3.2.2]nonane (Compound D79);

4-[5-(1-Methyl-2-indolyl)-1,3,4-oxadiazol-2-yl]-1,4-diazabicyclo[3.2.2]nonane (Compound D80);
4-[5-(2-Benzimidazolyl)-1,3,4-oxadiazol-2-yl]-1,4-diazabicyclo[3.2.2]nonane (Compound D81);
4-[5-(1-Methyl-2-benzimidazolyl)-1,3,4-oxadiazol-2-yl]-1,4-diazabicyclo[3.2.2]nonane (Compound D82);
4-[5-(2-Benzothiazolyl)-1,3,4-oxadiazol-2-yl]-1,4-diazabicyclo[3.2.2]nonane (Compound D83);
4-[5-(7-Phtalazinolinyl)-1,3,4-oxadiazol-2-yl]-1,4-diazabicyclo[3.2.2]nonane (Compound D84);
4-[5-(2-Quinazolinyl)-1,3,4-oxadiazol-2-yl]-1,4-diazabicyclo[3.2.2]nonane (Compound D85);
4-[5-(2-Quinoxalinyl)-1,3,4-oxadiazol-2-yl]-1,4-diazabicyclo[3.2.2]nonane (Compound D86);
4-[5-(1,8-Naphthyridin-2-yl)-1,3,4-oxadiazol-2-yl]-1,4-diazabicyclo[3.2.2]nonane (Compound D87);
4-[5-(1,8-Naphthyridin-3-yl)-1,3,4-oxadiazol-2-yl]-1,4-diazabicyclo[3.2.2]nonane (Compound D88);
4-[5-(2-Acridinyl)-1,3,4-oxadiazol-2-yl]-1,4-diazabicyclo[3.2.2]nonane (Compound D89);
4-[5-(3-Acridinyl)-1,3,4-oxadiazol-2-yl]-1,4-diazabicyclo[3.2.2]nonane (Compound D90);
4-[5-(2-Dibenzofuryl)-1,3,4-oxadiazol-2-yl]-1,4-diazabicyclo[3.2.2]nonane (Compound D91);
4-[5-(3-Dibenzofuryl)-1,3,4-oxadiazol-2-yl]-1,4-diazabicyclo[3.2.2]nonane (Compound D92);
4-[5-(2-Dibenzothienyl)-1,3,4-oxadiazol-2-yl]-1,4-diazabicyclo[3.2.2]nonane (Compound D93);
4-[5-(3-Dibenzothienyl)-1,3,4-oxadiazol-2-yl]-1,4-diazabicyclo[3.2.2]nonane (Compound D94);
4-[5-(2-Phenoxazinyl)-1,3,4-oxadiazol-2-yl]-1,4-diazabicyclo[3.2.2]nonane (Compound D95); and
4-[5-(3-Phenoxazinyl)-1,3,4-oxadiazol-2-yl]-1,4-diazabicyclo[3.2.2]nonane (Compound D96).

Example 2

In vitro Inhibition of $^3$H-α-Bungarotoxine Binding in Rat Brain

In this example the affinity of the compounds of the invention for binding to $α_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist.

$^3$H-α-Bungarotoxine labels nicotinic acetylcholine receptors formed by the $α_7$ subunit isoform found in brain and the $α_1$ isoform in the neuromuscular junction.

Tissue Preparation

Preparations are performed at 0–4° C. Cerebral cortices from male Wistar rats (150–250 g) are homogenised for 10 seconds in 15 ml of 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an IC$_{50}$ (the concentration of the test substance which inhibits the specific binding of $^3$H-α-bungarotoxin by 50%).

The results of these experiments are presented in Table 1 below.

TABLE 1

| Inhibition of $^3$H-α-Bungarotoxine Binding | |
|---|---|
| Compound No. | IC$_{50}$ (μM) |
| Compound 1A | 0.0067 |
| Compound D1 | 0.0058 |
| Compound D5 | 0.022 |

The invention claimed is:
1. A 1,4-diazabicycloalkane compound of Formula IV:

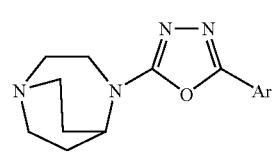

any of its enantiomers or any mixture of its enantiomers, or a pharmaceutically-acceptable addition salt thereof, or an N-oxide thereof, wherein Ar represents an aryl group selected from phenyl and naphthyl, or a heteroaryl group selected from furanyl, thienyl and pyridinyl, which aromatic group may optionally be substituted one or more times with substituents selected from the group consisting of alkyl, cycloalkyl, cycloalkyl-alkyl, alkenyl, alkynyl, alkoxy, alkoxy-alkyl, alkoxy-alkoxy, cycloalkoxy, cycloalkoxy-alkyl, cycloalkoxy-alkoxy, halogen, CF$_3$, CN, NO$_2$, NH$_2$, carboxy, carbamoyl, amido, sulfamoyl, phenyl and benzyl.

2. The compound of claim 1, wherein Ar may optionally be substituted one or more times with substituents selected from the group consisting of alkyl, alkoxy, halogen, CF$_3$, CN, NO$_2$, NH$_2$ and phenyl.

3. The compound of claim 1, wherein Ar represents phenyl, optionally substituted one or two times with substituents selected from the group consisting of alkyl, cycloalkyl, cycloalkyl-alkyl, alkoxy, cycloalleoxy, halogen, CF$_3$, CN, NO$_2$, NH$_2$ carboxy, carbamoyl, amido and sulfamoyl.

4. The compound of claim 1, which is
4-(5-Phenyl-1,3,4-oxadiazol-2-yl)-1,4-diazabicyclo[3.2.2]nonane;
4-[5-(3-Methoxyphenyl)-1,3,4-oxadiazol-2-yl]-1,4-diazabicyclo[3.2.2]nonane;
4-[5-(4-Merhoxyphenyl)-1,3,4-oxadiazol-2-yl]-1,4-diazabicyclo[3.2.2]nonane;
4-[5-(4-Chlorophenyl)-1,3,4-oxadiazol-2-yl]-1,4-diazabicyclo[3.2.2]nonane;

4-[5-(4-Phenyl-phenyl)-1,3,4-oxadiazol-2-yl]-1,4-diazabicyclo[3.2.2]nonane;

4-[5-(2-Naphthyl)-1,3,4-oxadiazol-2-yl]-1,4-diazabicyclo[3.2.2]nonane;

4-[5-(2-Furyl)-1,3,4-oxadiazol-2-yl]-1,4-diazabicyclo[3.2.2]nonane;

4-[5-(3-Pyridyl)-1,3,4-oxadiazol-2-yl]-1,4-diazabicyclo[3.2.2]nonaue;

4-[5-(4-Pyridyl)-1,3,4-oxadiazol-2-yl]-1,4-diazabicyclo[3.2.2]nonane; or

4-[5-(2-Tbienyl)-1,3,4-oxadiazol-2-yl]-1,4-diazabicyclo[3.2.2]nonane;

or an enantiomer or a mixture of enantiomers, or a pharmaceutically-acceptable addition salt thereot or an N-oxide thereof.

5. A pharmaceutical composition comprising a therapeutically effective amount of a compound of claim 1, any of its enantiomers or any mixture of its enantiomers, or a pharmaceutically-acceptable addition salt thereof, together with at least one pharmaceutically-acceptable carrier or diluent.

6. A method of the treatment or alleviation of a disease or a disorder or a condition of a living animal body, including a human, which disease or disorder is associated with withdrawal symptoms caused by termination of use of tobacco, heroin, cocaine, morphine, benzodiazepines, beuzodiazepine-like drugs, or alcohol, which method comprises the step of administering to such a living animal body, including a human, in need thereof a therapeutically effective amount of a compound of claim 1, any of its enantiomers or any mixture of its enantiomers, or a pharmaceutically-acceptable addition salt thereof.

7. The 1,4-diazabicycloalkane compound of clalm 1, wherein Ar represents phenyl, optionally substituted one or two times with substituents selected from the group consisting of alkyl, cycloalkyl, cycloalkyl-alkyl, alkoxy, cycloalkoxy, halogen, $CF_3$, CN, $NO_2$, $NH_2$, carboxy, carbamoyl, amido, sulfamoyl, phenyl, and benzyl.

8. The 1,4-diazabicycloalkane compound of claim 7, wherein Ar represents phenyl, optionally substituted one or two times with substituents selected fiom the group consisting of alkyl, alkoxy, halogen, $CF_3$, CN, $NO_2$, $NH_2$, and phenyl.

* * * * *